United States Patent
Kim et al.

(10) Patent No.: US 12,361,559 B2
(45) Date of Patent: Jul. 15, 2025

(54) METHOD AND SYSTEM FOR COMPUTING BLOOD FLOW VELOCITY BASED ON MEDICAL IMAGE

(71) Applicant: Medipixel, Inc., Seoul (KR)

(72) Inventors: Hyunwoo Kim, Seoul (KR); Sooncheol Noh, Seoul (KR); Si-Hyuck Kang, Seoul (KR)

(73) Assignee: Medipixel, Inc., Seoul (KR)

( * ) Notice: Subject to any disclaimer, the term of this patent is extended or adjusted under 35 U.S.C. 154(b) by 0 days.

(21) Appl. No.: 18/812,295

(22) Filed: Aug. 22, 2024

(65) Prior Publication Data
US 2024/0420331 A1    Dec. 19, 2024

Related U.S. Application Data

(63) Continuation of application No. PCT/KR2024/002383, filed on Feb. 23, 2024.

(30) Foreign Application Priority Data

Feb. 24, 2023   (KR) .................. 10-2023-0025426

(51) Int. Cl.
*G06K 9/00*      (2022.01)
*A61K 35/12*     (2015.01)
(Continued)

(52) U.S. Cl.
CPC .............. *G06T 7/0014* (2013.01); *G06T 7/20* (2013.01); *G06T 2207/30104* (2013.01)

(58) Field of Classification Search
CPC .. G06K 9/00; A61B 5/33; A61K 35/12; G06T 7/00

USPC ........ 382/100, 103, 106–107, 128–134, 156, 382/162, 168, 173, 181, 199, 214, 219, 382/224, 254, 274, 286–291, 305; 378/4, 378/21, 28, 64

See application file for complete search history.

(56) References Cited

U.S. PATENT DOCUMENTS 9,349,178 B1 *   5/2016   Itu ......................... A61B 8/06
2010/0034441 A1 * 2/2010  Makram-Ebeid ...... A61B 6/481
                                                      382/128
(Continued)

FOREIGN PATENT DOCUMENTS

JP    2019-022647 A    2/2019
JP    2021-525120 A    9/2021
(Continued)

*Primary Examiner* — Seyed H Azarian
(74) *Attorney, Agent, or Firm* — Banner & Witcoff, Ltd.

(57) ABSTRACT

A method comprises receiving a user input to select a first point and a second point from a medical image, extracting a plurality of blood vessel regions from a plurality of frame images of the medical image, determining a plurality of first regions associated with the first point and a plurality of second regions associated with the second point, determining a first frame image and a second frame image with the contrast agent arriving at the first point and the second point, based on a change in pixel intensity for each of the plurality of first regions and the plurality of second regions, and computing the blood flow velocity from the first point to the second point based on a time interval between the first frame image and the second frame image and on a distance between the first point and the second point.

20 Claims, 12 Drawing Sheets

(51) Int. Cl.
*G06T 7/00* (2017.01)
*G06T 7/20* (2017.01)

(56) References Cited

U.S. PATENT DOCUMENTS

| | | | |
|---|---|---|---|
| 2018/0330507 A1* | 11/2018 | Schormans | A61B 5/33 |
| 2019/0357778 A1 | 11/2019 | Wilson et al. | |
| 2019/0380593 A1* | 12/2019 | Bouwman | A61B 6/465 |
| 2020/0222018 A1* | 7/2020 | Van Walsum | A61B 6/5264 |
| 2022/0361834 A1* | 11/2022 | Butler | G16H 10/60 |
| 2023/0108647 A1 | 4/2023 | Tu et al. | |
| 2023/0306596 A1* | 9/2023 | Choi | A61B 5/7275 |
| 2023/0346330 A1* | 11/2023 | So | A61B 5/026 |
| 2023/0355196 A1 | 11/2023 | Kang et al. | |

FOREIGN PATENT DOCUMENTS

| | | |
|---|---|---|
| KR | 102195850 B1 | 12/2020 |
| KR | 102472963 B1 | 12/2022 |
| WO | 2021-175039 A1 | 9/2021 |

* cited by examiner 910  920  930

METHOD AND SYSTEM FOR COMPUTING BLOOD FLOW VELOCITY BASED ON MEDICAL IMAGE

CROSS-REFERENCE TO RELATED APPLICATION

This application is a continuation of International Patent Application No. PCT/KR2024/002383, filed on Feb. 23, 2024, which is based upon and claims the benefit of priority to Korean Patent Application No. 10-2023-0025426, filed on Feb. 24, 2023. The disclosures of the above-listed applications are hereby incorporated by reference herein in their entirety.

BACKGROUND

Field

The present disclosure relates to a method for computing a blood flow velocity based on a medical image, and specifically, to a method and system for computing a blood flow velocity from first to second points selected from the medical image.

Description of Related Art

In recent medical fields, uses of 2D images acquired with X-rays, CT scans, cardiovascular angiography, etc. for the diagnosis of lesions or for reading images by reconstructing the 2D images into 3D images and visualizing the 2D images in an easy-to-understand manner are increased.

In addition, a product was developed, which analyzes 3D images and automatically calculates the blood flow velocity in the cardiovascular system. The blood flow velocity acts as an important factor in calculating pressure loss and accurately measuring the blood flow velocity, which is important in accurately diagnosing the lesion and accurately establishing a treatment plan.

Existing products for measuring blood flow velocities calculate the average blood flow velocity in the cardiovascular system. However, the cardiovascular system may include bifurcation at which a main blood vessel branches off to branch blood vessels, and the blood flow velocity may change as the blood flow changes in these branches. That is, the blood flow velocity around the branch may be relatively faster than the average blood flow velocity. Accordingly, if the cardiovascular blood flow velocity is computed based on the average velocity, there can be a wide gap between the actual blood flow velocity in the branch and the average blood flow velocity in the cardiovascular system.

The blood flow velocity in specific sections in the cardiovascular system can be used as a major factor in accurately diagnosing lesions and establishing treatment plans, but the related products cannot compute the blood flow velocity for the specific sections of blood vessels.

Accordingly, there is a need for a product that can accurately compute the blood flow velocity for a specific section of the blood vessel.

SUMMARY

In order to solve one or more problems (e.g., the problems described above and/or other problems not explicitly described herein), the present disclosure provides a method for computing a blood flow velocity based on a medical image, a computer program stored in a recording medium, and an apparatus (system) including the same.

According to an aspect of the present disclosure, a method for computing a blood flow velocity may be performed by one or more processors and may comprise receiving a user input to select a first point and a second point from a medical image obtained by capturing an image of a blood vessel injected with a contrast agent, extracting a plurality of blood vessel regions from a plurality of frame images included in the medical image, determining, in the extracted plurality of blood vessel regions, a plurality of first regions associated with the first point and a plurality of second regions associated with the second point, determining, among the plurality of frame images, a first frame image with the contrast agent arriving at the first point, based on a change in pixel intensity for each of the plurality of first regions, determining, among the plurality of frame images, a second frame image with the contrast agent arriving at the second point, based on a change in pixel intensity for each of the plurality of second regions, and computing the blood flow velocity from the first point to the second point based on a time interval between the first frame image and the second frame image and on a distance between the first point and the second point.

According to an aspect of the present disclosure, the extracting the plurality of blood vessel regions from the plurality of frame images may comprise identifying, among the plurality of frame images included in the medical image, a frame image having the selected first and second points, determining that, among the entire frame images included in the medical image, a plurality of frame images numbered as or lower than a number corresponding to the identified frame image are target images for analysis, and extracting the plurality of blood vessel regions from at least some of the plurality of frame images determined to be the target images for analysis.

According to an aspect of the present disclosure, the determining that the plurality of frame images are the target images for analysis may comprise sampling a plurality of frame images numbered as or lower than a number corresponding to the identified frame image, and determining that the plurality of sampled frame images are the target images for analysis.

According to an aspect of the present disclosure, the extracting the plurality of blood vessel regions from the plurality of frame images may comprise applying each of the plurality of frame images to a machine learning model to extract the plurality of blood vessel regions, and the machine learning model may be configured to perform an operation based on supervised learning for a highest-numbered frame image of the plurality of frame images, and perform an operation based on semi-supervised learning for a frame image numbered lower than the highest-numbered frame image.

According to an aspect of the present disclosure, the applying each of the plurality of frame images to the machine learning model to extract the plurality of blood vessel regions may comprise applying the highest-numbered frame image of the plurality of frame images to the machine learning model to extract a blood vessel region included in the highest-numbered frame image, sequentially determining that, based on an order of higher number, each of a plurality of frame images numbered lower than the highest-numbered frame image is a target frame image to be applied, and applying, to the machine learning model, at least one blood vessel region extracted from each of at least one or more frame images numbered higher than the determined target frame image, and the determined target frame image, and the machine learning model may be configured to extract the blood vessel region from the target frame image based on at least one blood vessel region extracted from each of at least one or more frame images numbered higher the target frame image.

According to an aspect of the present disclosure, the applying the at least one blood vessel region and the determined target frame image to the machine learning model may comprise selecting, among the frame images numbered higher the target frame image, at least one frame image included in a predetermined frame range or in a predetermined number of frame images, and applying, to the machine learning model, the at least one blood vessel region extracted from each of the at least one or more selected frame images.

According to an aspect of the present disclosure, the method may further comprise correcting at least one of the plurality of frame images such that blood vessel regions included in each of the plurality of frame images are positioned within a threshold distance range, prior to the determining the first frame image with the contrast agent arriving at the first point.

According to an aspect of the present disclosure, the correcting the at least one of the plurality of frame images may comprise computing a spatial characteristic value for each of the plurality of frame images, and correcting at least one frame image such that a difference in spatial characteristic values between adjacent frame images is equal to or less than a predetermined threshold value.

According to an aspect of the present disclosure, the correcting the at least one of the plurality of frame images may comprise applying, to the machine learning model, the plurality of frame images to correct at least one of the plurality of frame images, and the machine learning model may be configured to correct at least one frame image such that a difference in spatial characteristic values between adjacent frame images is equal to or less than a predetermined threshold value.

According to an aspect of the present disclosure, the determining the first frame image with the contrast agent arriving at the first point may comprise computing a change in pixel intensity for the first region determined in each of the plurality of frame images, and determining that, based on the computed change in pixel intensity for the first region, a frame image showing a predetermined size of change in pixel intensity is the first frame image.

According to an aspect of the present disclosure, the determining that the frame image showing the predetermined size of change in pixel intensity is the first frame image may comprise generating a first graph associated with the change in pixel intensity for the first region, converting the first graph into a second graph based on at least one of a zeroth-order term or a first-order term, identifying a point at which a pixel value rises for the first time in the second graph, and determining that a frame image associated with the identified rising point is the first frame image.

According to an aspect of the present disclosure, the determining the plurality of first regions associated with the first point and the plurality of second regions associated with the second point may comprise determining that a first-sized corresponding region including the first point is each of the plurality of first regions, and determining that a second-sized corresponding region including the second point is each of the plurality of second regions.

According to an aspect of the present disclosure, a method for extracting a blood vessel region may be performed by one or more processors and may comprise receiving a medical image obtained by capturing an image of a blood vessel injected with a contrast agent, determining a plurality of frame images for analysis from the medical image, and applying the plurality of frame images to a machine learning model to extract a plurality of blood vessel regions from the plurality of frame images, and the machine learning model may be configured to perform an operation based on supervised learning for a highest-numbered frame image of the plurality of frame images to extract a blood vessel region, and perform an operation based on semi-supervised learning for a frame image numbered lower than the highest-numbered frame image to extract a blood vessel region.

According to an aspect of the present disclosure, the extracting the plurality of blood vessel regions from the plurality of frame images may comprise applying the highest-numbered frame image of the plurality of frame images to the machine learning model to extract a blood vessel region included in the highest-numbered frame image, sequentially determining that, based on an order of higher number, each of a plurality of frame images numbered lower than the highest-numbered frame image is a target frame image to be applied, and applying, to the machine learning model, at least one blood vessel region extracted from each of at least one or more frame images numbered higher than the determined target frame image, and the determined target frame image, and the machine learning model may be configured to extract the blood vessel region from the target frame image based on at least one blood vessel region extracted from each of at least one or more frame images numbered higher the target frame image.

According to an aspect of the present disclosure, a computer program stored in a computer-readable recording medium for causing performance of the method for computing a blood flow velocity is provided.

According to an aspect of the present disclosure, an information processing system may comprise a memory and one or more processors connected to the memory and configured to execute one or more computer-readable programs included in the memory, and the one or more programs may include instructions for receiving a user input to select a first point and a second point from a medical image obtained by capturing an image of a blood vessel injected with a contrast agent, extracting a plurality of blood vessel regions from a plurality of frame images included in the medical image, determining, in the extracted plurality of blood vessel regions, a plurality of first regions associated with the first point and a plurality of second regions associated with the second point, determining, among the plurality of frame images, a first frame image with the contrast agent arriving at the first point, based on a change in pixel intensity for each of the plurality of first regions, determining, among the plurality of frame images, a second frame image with the contrast agent arriving at the second point, based on a change in pixel intensity for each of the plurality of second regions, and computing the blood flow velocity from the first point to the second point based on a time interval between the first frame image and the second frame image and on a distance between the first point and the second point.

According to some aspects of the present disclosure, the blood flow velocity from the first to the second points selected by the user from the entire section of the blood vessel can be accurately computed. Accordingly, the user can conveniently check the blood flow velocity of the section desired by the user.

According to some aspects of the present disclosure, the machine learning model trained by semi-supervised learning may be used to accurately extract a plurality of blood vessel regions from a plurality of frame images included in the medical image.

According to some aspects of the present disclosure, at least one of the plurality of frame images may be corrected such that a plurality of blood vessel regions included in the plurality of frame images are positioned within a threshold distance range. Accordingly, a plurality of blood vessel regions included in the plurality of frame images are aligned, so that the blood flow velocity may be more accurately computed.

According to some aspects of the present disclosure, the frame image with the first point and the second point selected from the medical image may be identified, and once the frame image is identified, subsequent frame images may be removed from the frame images for analysis. Accordingly, the frame image not required for analysis can be removed from the medical image, improving the image analysis speed and reducing the computing resources for image analysis.

According to some aspects of the present disclosure, based on the change in pixel intensity of the blood vessel region, a time point at which the contrast agent arrives at the first point, and a time point at which the contrast agent arrives at the second point can be accurately measured.

The effects of the present disclosure are not limited to the effects described above, and other effects not described herein can be clearly understood by those of ordinary skill in the art (referred to as "ordinary technician") from the description of the claims.

BRIEF DESCRIPTION OF THE DRAWINGS

The above and other objects, features and advantages of the present disclosure will be described with reference to the accompanying drawings described below, where similar reference numerals indicate similar elements, but not limited thereto, in which.

DETAILED DESCRIPTION

Figure 1:
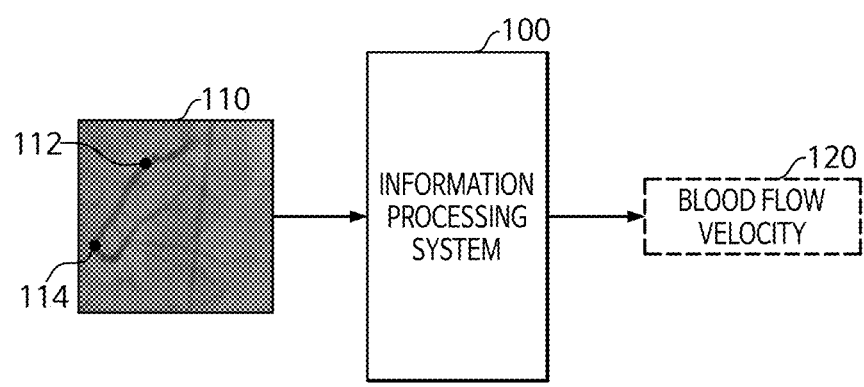
FIG. 1 is a diagram illustrating an example of an information processing system that computes a blood flow velocity at two points selected from a medical image.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Accordingly, the terms used in this disclosure should be defined based on the meaning of the term and the overall content of the present disclosure, rather than simply the name of the term.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it is intended as meaning that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

A "module" or "unit" may be implemented as a processor and a memory, or may be implemented as a circuit (circuitry). Terms such as circuit and circuitry may refer to circuits in hardware, but may also refer to circuits in software. The "processor" should be interpreted broadly to encompass a general-purpose processor, a central processing unit (CPU), a microprocessor, a digital signal processor (DSP), a neural processing unit (NPU), a controller, a microcontroller, a state machine, etc. Under some circumstances, the "processor" may refer to an application-specific integrated circuit (ASIC), a programmable logic device (PLD), a field-programmable gate array (FPGA), etc. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, etc. The memory is said to be in electronic communication with a processor if the processor can read information from and/or write information to the memory. The memory integrated with the processor is in electronic communication with the processor.

In the present disclosure, a "system" may refer to at least one of a server apparatus and a cloud apparatus, but is not limited thereto. For example, the system may include one or more server apparatus. In another example, the system may include one or more cloud apparatus. In still another example, the system may include both the server apparatus and the cloud apparatus operated in conjunction with each other.

In addition, terms such as first, second, A, B, (a), (b), etc. used in the following examples are only used to distinguish certain components from other components, and the nature, sequence, order, etc. of the components are not limited by the terms.

In addition, in the following examples, if a certain component is stated as being "connected," "combined" or "coupled" to another component, it is to be understood that there may be yet another intervening component "connected," "combined" or "coupled" between the two components, although the two components may also be directly connected or coupled to each other.

In addition, as used in the following examples, "comprise" and/or "comprising" does not foreclose the presence or addition of one or more other elements, steps, operations, and/or devices in addition to the recited elements, steps, operations, or devices.

In the present disclosure, "each of a plurality of A" may refer to each of all components included in the plurality of A, or may refer to each of some of the components included in a plurality of A.

Before describing various examples of the present disclosure, terms used herein will be explained.

Throughout the description, a "medical image" may refer to a picture and/or an image captured for diagnosis, treatment, and prevention of a disease, and may refer to a picture and/or an image captured inside/outside the patient's body. Examples of the medical image may include pictures and/or images of all modalities, such as X-ray images, ultrasound images, chest radiograph, computed tomography (CT), positron emission tomography (PET), magnetic resonance imaging (MRI), sonography (ultrasound, US), functional magnetic resonance imaging (fMRI), digital pathology whole slide image (WSI), digital breast tomosynthesis (DBT), etc. In some examples, the "medical image" may refer to a plurality of frame images included in the medical image. In addition, in some examples, the "medical image" may include a medical image obtained by capturing an image of a blood vessel of a patient who has been administered the contrast agent.

Throughout the description, the "frame image" may refer to still images included in the medical image. In some examples, each of the plurality of frame images included in the medical image may be sequentially assigned a frame number (e.g., frame image #1, frame image #2, . . . , frame image #n, and so on) according to the order in which the medical image was captured.

Throughout the description, a "machine learning model" may include any model that is used to infer an answer to a given input. The machine learning model may include an artificial neural network model including an input layer, a plurality of hidden layers, and an output layer. In an example, each layer may include one or more nodes. In addition, the machine learning model may include weights associated with a plurality of nodes included in the machine learning model. In an example, the weights may include any parameter associated with the machine learning model. Throughout the description, the machine learning model may refer to an artificial neural network model, and the artificial neural network model may refer to the machine learning model. The machine learning model herein may be a model trained with various learning methods. For example, various learning methods such as supervised learning, semi-supervised learning, unsupervised learning, reinforcement learning, etc. may be used.

Throughout the description, "learning (training)" may refer to any process of changing weights associated with the machine learning model using training data, ground-truth labels or/and reference labels. Learning (training) as used herein may refer to a process of changing or updating weights associated with the machine learning model through one or more of forward propagation and backward propagation of the machine learning model by using the training images and the ground-truth labels (e.g., masked regions or masked images).

Throughout the description, "each of a plurality of A's" may refer to each of all components included in the plurality of A's, or may refer to each of some of the components included in a plurality of A's. For example, each of a plurality of frame images may refer to each of all frame images included in the plurality of frame images, or to each of some frame images included in the plurality of frame images.

Hereinafter, various aspects of the present disclosure will be described in detail with reference to the accompanying drawings.

FIG. 1 is a diagram illustrating an example of an information processing system 100 that computes a blood flow velocity at two points 112 and 114 selected from a medical image 110. As illustrated in FIG. 1, the information processing system 100 may receive the medical image 110 and select a plurality of frames for analysis from among a plurality of frame images included in the received medical image 110. In addition, the information processing system 100 may analyze the plurality of selected frame images to compute a blood flow velocity 120 from the first to the second points 112 to 114 and output the computed result. In this case, the first point 112 may be a proximal point, and the second point 114 may be a distal point.

The information processing system 100 may output the computed blood flow velocity 120 through the display means. Additionally or alternatively, the information processing system 100 may transmit the computed blood flow velocity 120 to a user terminal.

While the information processing system 100 is illustrated as one computing device in FIG. 1, aspects are not limited thereto, and the information processing system 100 may be configured to process information and/or data in a distributed manner through a plurality of computing devices. The information processing system 100 may be any computing device used to compute the blood flow velocities of the two selected points 112 and 114 of the medical image 110. In an example, the computing device may refer to any type of device equipped with a computing function, and may be a notebook, a desktop, a laptop, a server, a cloud system, etc., for example, but is not limited thereto.

Although a storage system capable of communicating with the information processing system 100 is not illustrated in FIG. 1, the information processing system 100 may be connected to or configured for communication with one or more storage systems. The storage system connected to or configured for communication with the information processing system 100 may be a device or cloud system that stores and manages various data associated with the computation of blood flow velocities. For efficient data management, the storage system may store and manage various types of data using a database. In this case, the various types of data may include any data associated with computing blood flow velocities, and for example, the various types of data may include machine learning models, medical images, etc., but are not limited thereto.

The information processing system 100 may receive the medical image 110 obtained by capturing an image of a blood vessel of the patient who has been administered the contrast agent. This medical image 110 may be received through a communication-enabled storage medium (e.g., a hospital system, a local/cloud storage system, etc.). The information processing system 100 may analyze a plurality of frame images included in the received medical image 110 to compute a blood flow velocity from the first to the second points 112 to 114 selected from the medical image 110.

The information processing system 100 may extract a plurality of blood vessel regions from a plurality of frame images included in the medical image 110 and determine a plurality of first regions associated with the first point 112 and a plurality of second regions associated with the second point 114 from the extracted plurality of blood vessel regions. The blood vessel region may be a region in which the contrast agent is administered. In addition, the information processing system 100 may determine, among the plurality of frame images, a first frame image with the contrast agent arriving at the first point 112, based on a change in pixel intensity for each of the plurality of first regions. In this case, the first frame image with the contrast agent arriving at the first point 112 may refer to, among the plurality of frame images, a frame image with the contrast agent appearing first time in the first region. Additionally, the information processing system 100 may determine, among the plurality of frame images, a second frame image with the contrast agent arriving at the second point 114, based on a change in pixel intensity for each of the plurality of second regions. In this case, the second frame image with the contrast agent arriving at the second point 114 may refer to, among the plurality of frame images, a frame image with the contrast agent appearing first time in the first region.

The information processing system 100 may compute a blood flow velocity from the first point to the second point based on a time interval between the first frame image and the second frame image and a distance between the first point and the second point. Accordingly, if a user (e.g., a doctor, etc.) selects a specific section from the medical image, a blood flow velocity for the specific section may be computed and provided to the user.

Figure 2:
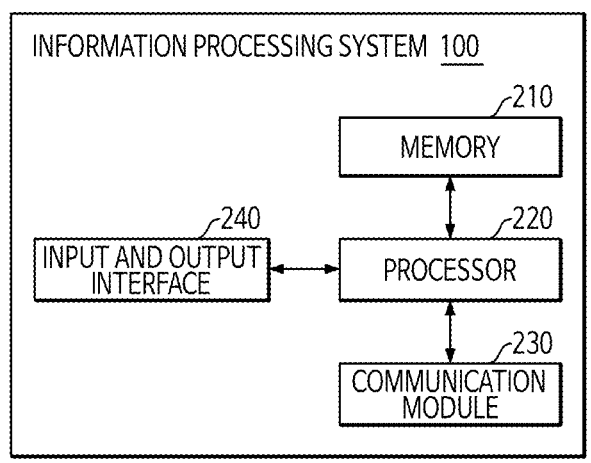
FIG. 2 is a block diagram illustrating an internal configuration of the information processing system.

FIG. 2 is a block diagram illustrating an internal configuration of the information processing system 100. The information processing system 100 may include a memory 210, a processor 220, a communication module 230, and an input and output interface 240. As illustrated in FIG. 2, the information processing system 100 may be configured to communicate information and/or data through a network by using the communication module 230.

The memory 210 may include any non-transitory computer-readable recording medium. The memory 210 may include a permanent mass storage device such as read only memory (ROM), disk drive, solid state drive (SSD), flash memory, etc. In another example, a non-destructive mass storage device such as ROM, SSD, flash memory, disk drive, etc. may be included in the information processing system 100 as a separate permanent storage device that is distinct from the memory. In addition, an operating system and at least one program code (e.g., code for computing blood flow velocity, etc.) may be stored in the memory 210. In FIG. 2, the memory 210 is illustrated as a single memory, but this is only for convenience of description, and the memory 210 may include a plurality of memories.

These software components may be loaded from a computer-readable recording medium separate from the memory 210. Such a separate computer-readable recording medium may include a recording medium directly connectable to the information processing system 100, and may include a computer-readable recording medium such as a floppy drive, a disk, a tape, a DVD/CD-ROM drive, a memory card, etc., for example. In another example, the software components may be loaded into the memory 210 through the communication module 230 rather than the computer-readable recording medium. For example, at least one program may be loaded into the memory 210 based on a computer program (e.g., a program for computing blood flow velocities, etc.) installed by the files provided by the developers, or by a file distribution system that distributes an installation file of an application through the communication module 230.

The communication module 230 may provide a configuration or function for the user terminal and/or an external device and the information processing system 100 to communicate with each other through a network, and may provide a configuration or function for the information processing system 100 to communicate with an external system (e.g., a separate cloud system).

In addition, the input and output interface 240 of the information processing system 100 may be a means for interfacing with a device (not illustrated) for inputting or outputting, which may be connected to, or included in the information processing system 100. For example, the input and output interface 240 may include at least one of a PCI express interface and an Ethernet interface. In FIG. 2, the input and output interface 240 is illustrated as a component configured separately from the processor 220, but aspects are not limited thereto, and the input and output interface 240 may be configured to be included in the processor 220. The information processing system 100 may include more components than those illustrated in FIG. 2.

The processor 220 may be configured to process the commands of the computer program by performing basic arithmetic, logic, and input and output operations. The processor 220 may receive a user input to select a first point and a second point from a medical image obtained by capturing an image of a blood vessel after contrast agent administration. In this case, the processor 220 may be configured to process instructions for extracting a plurality of blood vessel regions from a plurality of frame images included in the medical image and determining a plurality of first regions associated with the first point and a plurality of second regions associated with the second point in the extracted plurality of blood vessel regions. Additionally, the processor 220 may be configured to process instructions for determining, among the plurality of frame images, the first frame image with the contrast agent arriving at the first point, based on the change in pixel intensity for each of the plurality of first regions, and determining, among the plurality of frame images, the second frame image with the contrast agent arriving at the second point, based on the change in pixel intensity for each of the plurality of second regions. In addition, the processor 220 may be configured to process instructions for computing the blood flow velocity from the first point to the second point based on the time interval between the first frame image and the second frame image and the distance between the first point and the second point.

Figure 3:
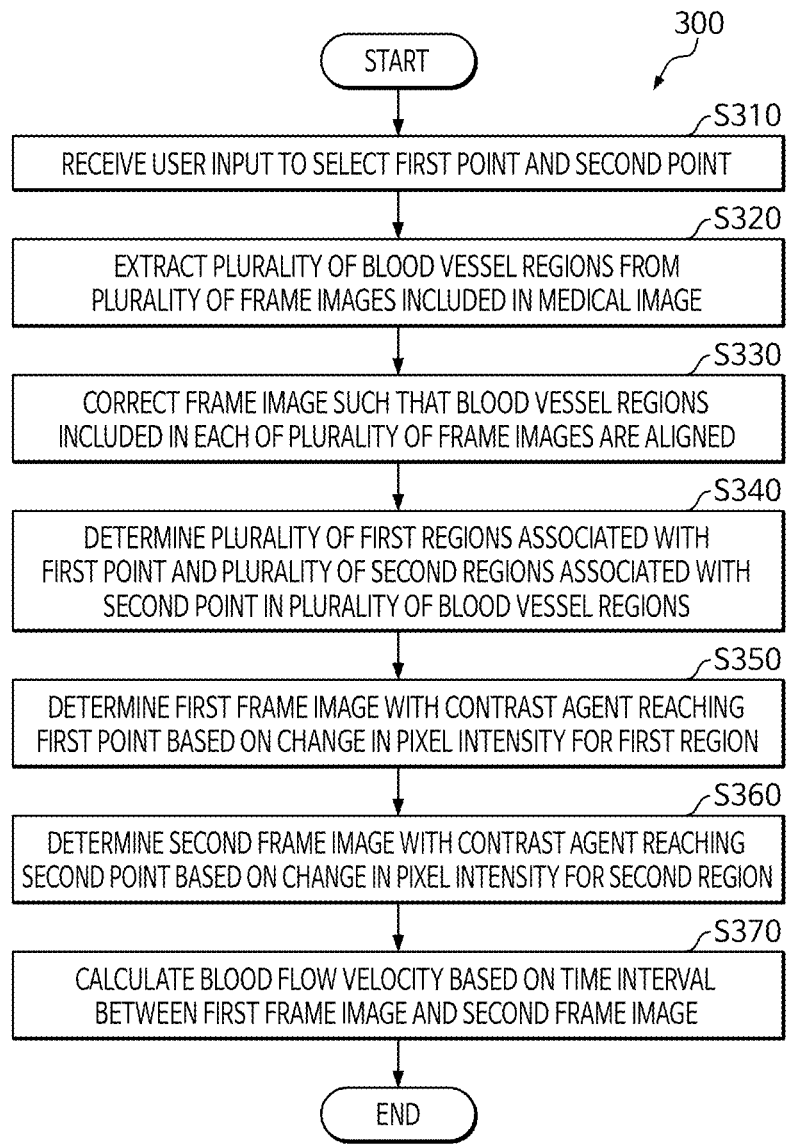
FIG. 3 is a flowchart provided to explain a method for computing a blood flow velocity based on a medical image.

FIG. 3 is a flowchart provided to explain a method 300 for computing a blood flow velocity based on a medical image. The method illustrated in FIG. 3 is merely one example for achieving the object of the present disclosure, and it goes without saying that certain steps of operations may be added or omitted as needed. In addition, the method illustrated in FIG. 3 may be performed by one or more processors included in the information processing system. For convenience of description, it will be described that each step of operation illustrated in FIG. 2 is performed by the processor included in the information processing system illustrated in FIG. 2.

The processor may receive a user input to select first and second points from a medical image obtained by capturing an image of a blood vessel after contrast agent injection, at S310. For example, while the medical image obtained by capturing the image of the blood vessel after contract agent injection is displayed via a display means, user may select two points in the blood vessel in the medical image while changing the frame images included in the medical image (i.e., while changing the frame image being played back) using a mouse, touch screen, etc. If two points are selected from the medical image, the processor may acquire, through an input and output interface or a communication module, the coordinates of the first point, the coordinates of the second point, and the numbers of the frame images having the selected two points.

The processor may extract a plurality of blood vessel regions from a plurality of frame images included in the medical image, at S320. The processor may apply a plurality of frame images to a machine learning model that performs operations based on supervised learning and/or semi-supervised learning to extract a plurality of blood vessel regions. A specific method for extracting a plurality of blood vessel regions using a machine learning model will be described below with reference to FIG. 4.

The processor may correct at least one frame image such that blood vessel regions included in each of the plurality of frame images are aligned, at S330. The processor may correct at least one of the plurality of frame images such that the blood vessel regions included in each of the plurality of frame images are positioned at a distance within a threshold distance range. Details of the method for correcting the frame image will be described in detail below with reference to FIGS. 7 to 10.

The processor may determine, among a plurality of blood vessel regions, a plurality of first regions associated with the first point and a plurality of second regions associated with the second point, at S340. For example, each frame image includes a blood vessel region, and the processor may determine the first region and the second region from the blood vessel region included in each frame image. The processor may determine a plurality of first regions based on a region including the first point and corresponding to the first size, and determine the second region based on a region including the second point and corresponding to the second size. For example, among a plurality of blood vessel regions, the processor may determine the first region based on a circle having a predetermined radius around the first point, and determine the second region based on a circle having a predetermined radius around the second point. As another example, the processor may compute a midpoint based on the first point and the second point, cover a Gaussian kernel based on the midpoint, apply a higher weight to the pixel closer to the midpoint, and determine the first region and the second region associated with the blood vessel based on the plurality of weighted pixels.

The processor may determine, among the plurality of frame images, a first frame image with the contrast agent arriving at the first point, based on a change in pixel intensity for each of the plurality of first regions, at S350.

In addition, the processor may determine, among the plurality of frame images, a second frame image with the contrast agent arriving at the second point, based on a change in pixel intensity for each of a plurality of second regions, at S360. Details of the method for determining the frame image with the contrast agent arriving at the points based on the change in pixel intensity will be described below in detail with reference to FIGS. 10 and 11.

The processor may compute a blood flow velocity from the first point to the second point based on a time interval between the first frame image and the second frame image and a distance between the first point and the second point, at S370. The process may compute the time interval between the first frame image and the second frame image based on the frame number of the first frame image, the frame number of the second frame image, and the number of frames per second. In addition, the process may compute a pixel-based distance between the first point and the second point based on pixels based on the first pixel coordinates associated with the first point and the first pixel coordinates associated with the second point, and apply a correction value to the computed pixel-based distance to compute the actual distance between the first point and the second point. The correction value may be determined based on the expansion or reduction ratio of the medical image.

Figure 4:
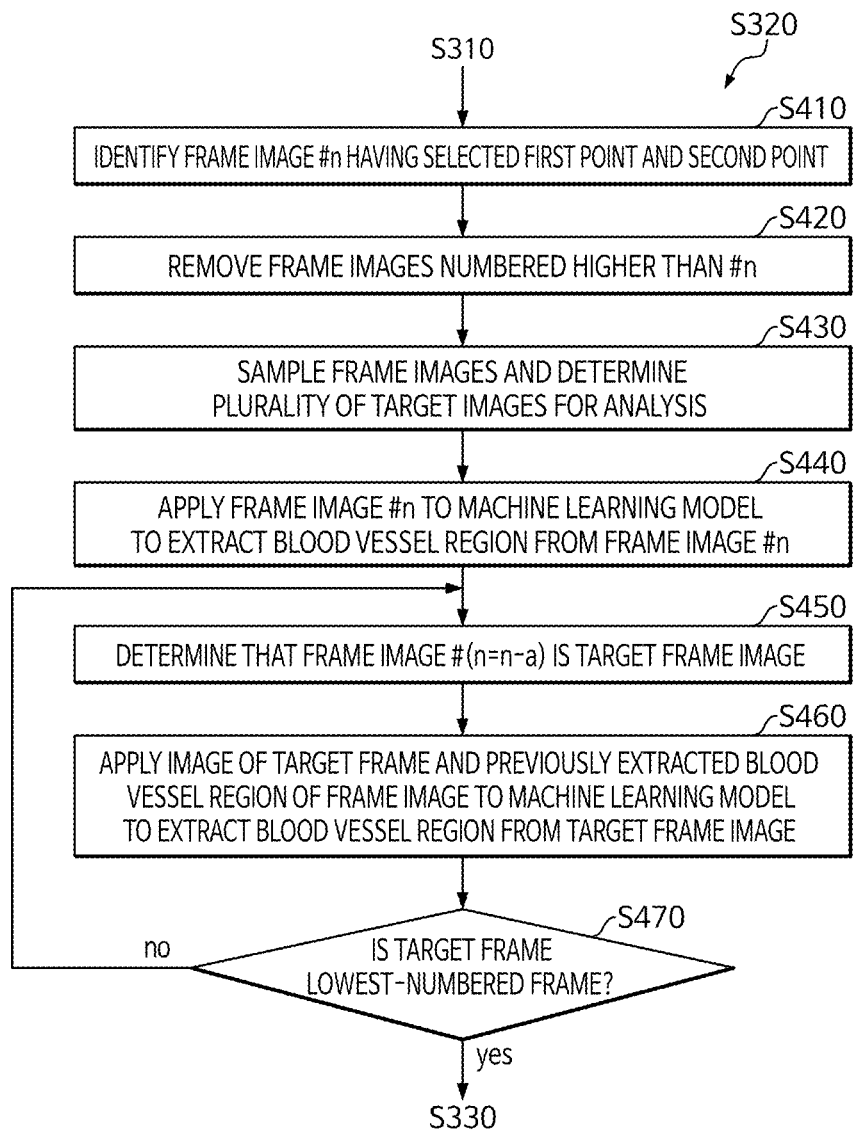
FIG. 4 is a flowchart provided to explain the operation S320 of FIG. 3 in more detail.

FIG. 4 is a flowchart provided to explain the operation S320 of FIG. 3 in more detail. The processor may identify a frame image #n having the selected first and second points from the medical image, at S410. Here, #n may refer to the number of the frame image having the selected first and second points.

The processor may remove the frame images numbered higher than the frame image #n from the medical image to filter the frame images included in the medical image, at S420. For example, if the medical image includes frame images #0 to #99 and user (e.g., medical staff) selects the first point and the second point in the frame image #80, the frame images #81 to #99 may be removed from the medical image. It is to be understood that removing the images from the medical image refers to, rather than modifying the medical image itself, determining that the medical image resulting from removing the frame images #81 to #99 from the original medical image is a medical image for analysis. The frame images numbered higher than the frame image number having the selected first and second points may be removed from the medical image for analysis, because the blood flow velocity is analyzed correctly even if those frame images are removed.

In addition, while playing back the medical image, the user may visually identify the blood vessel region in the frame image with the blood vessel clearly visible with the contrast agent arriving there, and select the first point and the second point from the identified blood vessel region. In the frame images numbered higher than the frame image having the selected first and second points, the blood vessel region including the first point and the second point may be clearly visible because the contrast agent continuously moves along the blood vessel. That is, the frame image #n having the selected first and second points, and the frame image numbered higher than #n may have substantially the same pixel intensity in the first region associated with the first point and the second region associated with the second point.

Accordingly, both the blood flow velocity computed by analyzing the frame images numbered as or lower than frame image #n, and the blood flow velocity computed by analyzing all the frame images included in the original medical image may be the same as each other. For this reason, performing analysis on the frame images numbered as or lower than the frame image #n having the selected first and second points may derive the same result as the result of analyzing all the frame images. Besides, speed may be improved, and computing resources may be reduced.

The processor may sample the frame images numbered as or lower than the frame image #n and determine a plurality of target images for analysis, at S430. In this case, the processor may sample the frame images with numbers at predetermined interval. For example, the process may sample frame images with numbers corresponding to a specific multiple.

The processor may apply the frame image #n to a pre-trained machine learning model to extract the blood vessel region from the frame image #n, at S440. The machine learning model may be a model trained based on a plurality of training data sets. The plurality of training data sets may include a plurality of pieces of training data and a plurality of ground-truth labels. The training data may be a frame image, and the ground-truth label may be a blood vessel region included in the frame image. The machine learning model may analyze training data and output a blood vessel region. A loss between the blood vessel region output from the machine learning model and the blood vessel region included in the ground-truth label may be computed, and the computed loss may be fed back to the machine learning model such that the weight of at least one node included in the machine learning model may be adjusted.

The machine learning model may be configured to perform an operation based on supervised learning for a highest-numbered frame image of the frame images, and perform an operation based on semi-supervised learning for the frame images numbered lower than the highest-numbered frame image. For example, at S440, since the frame image #n is the highest-numbered image among the sampled frame images, the machine learning model may perform an operation based on supervised learning on the frame image #n and extract the blood vessel region from the highest-numbered frame image.

The processor may subtract a natural number a from n to update n, and may determine that the updated frame image #n is the target frame image, at S450. For example, if n is 100 and a is 3, the updated n may be 97. In this case, the size of subtracted a may be determined based on the sampling interval.

The processor may apply the image of the target frame and at least one previously extracted blood vessel region to the machine learning model to extract a blood vessel region from the target frame image, at S460. The machine learning model may perform an operation based on semi-supervised learning on the frame images numbered lower than the highest-numbered frame image to extract a blood vessel region from the frame images numbered lower than the highest-numbered frame image. For example, the machine learning model may extract the blood vessel region from the frame images numbered lower than the highest-numbered frame image, using the blood vessel region extracted from the highest-numbered frame image as a reference label. For example, if #100 is the highest frame number and #97 is the second highest frame number of the sampled and extracted frame images, the blood vessel region extracted from the frame image #97 and the frame image #100 may be applied to the machine learning model, and the machine learning model may extract the blood vessel region from the frame image #97 using the blood vessel region extracted from frame image #100 as a reference label.

The processor may determine whether the currently determined target frame image is a lowest-numbered frame image, at S470. The processor may repeat the processes from S450 in response to the determination that the currently determined target frame image is not the lowest-numbered frame image. If the processes are repeated from S450, it may be determined that all sampled frame images are target image frames, and a blood vessel region may be extracted from each of the sampled images. At least one blood vessel region and a target frame image extracted from each of the at least one frame image with a larger number than the target frame image may be applied to the machine learning model, and the machine learning model may perform an operation based on semi-supervised learning on the target frame image and the at least one blood vessel region to extract the blood vessel region from the target frame image. For example, if the sampled frame has the frame image numbers #100, #97, #94, #91, . . . , #0, and if the frame image #91 is determined to be the target frame image, the processor may apply the blood vessel region extracted from the frame image #100, the blood vessel region extracted from the frame image #97, the blood vessel region extracted from the frame image #94, and the frame image #91 to the machine learning model to extract the blood vessel region included in the frame image #91.

Figure 5:
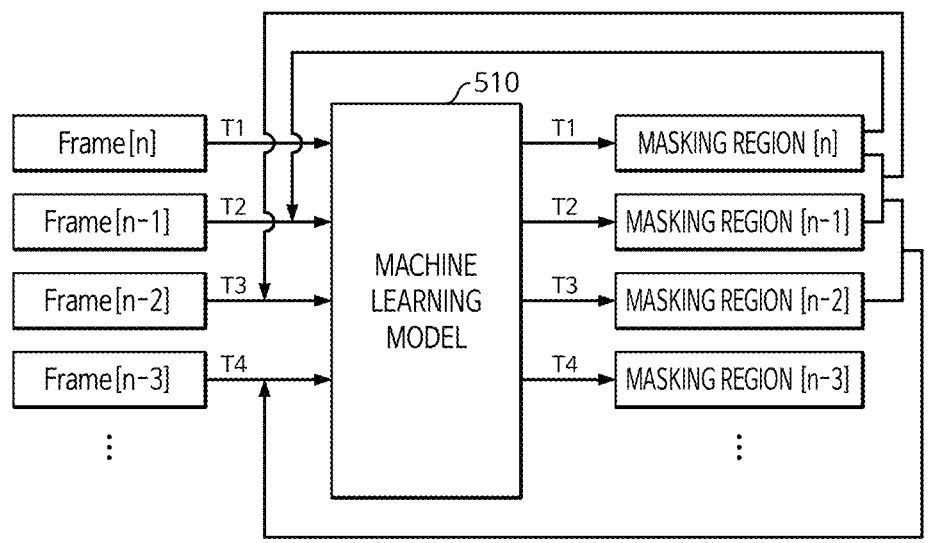
FIG. 5 illustrates an example of a machine learning model.

FIG. 5 illustrates an example of a machine learning model 510. In FIG. 5, a masking region may be associated with the blood vessel region. For example, the blood vessel region extracted from the frame image may be masked in the frame image.

As illustrated in FIG. 5, the highest-numbered frame image (Frame[n]) may be applied as the target frame image to the machine learning model 510 during a period T1, and the machine learning model 510 may output a masking region [n] associated with the blood vessel region extracted from the frame image (Frame[n]) during the period T1. In this case, the machine learning model 510 may perform an operation based on supervised learning on the frame image (Frame[n]) to output the masking region [n].

During a subsequent period T2, the target frame image (Frame[n−1]) and the masking region [n] extracted during the period T1 may be applied to the machine learning model 510, and the machine learning model 510 may analyze the frame image ([n−1]) during the period T2 to output a masking region [n−1]. In this case, the machine learning model 510 may use the masking region [n] as a reference label to perform an operation based on semi-supervised learning to extract and output the masking region [n−1] from the frame image (Frame[n−1]).

During a subsequent period T3, a target frame image Frame[n−2], the masking region[n] extracted during the period T1, and the masking region[n−1] extracted during the period T2 may be applied to the machine learning model 510, and the machine learning model 510 may analyze the frame image Frame[n−2] and output the masking region[n−2]from the frame image Frame[n−2] during the period T3. In this case, the machine learning model 510 may use the masking region [n] and the masking region [n−1] as reference labels and perform operations based on semi-supervised learning on the frame image (Frame[n−2]) to output the masking region [n−1].

During a period that follows the period T3, the next frame image (Frame[n−3], . . . ) may be sequentially determined to be a target frame image, the determined target frame image may be applied to the machine learning model 510, and at least one masking region already output by the machine learning model 510 may be applied to the machine learning model together with the target frame image.

According to some aspects, the number of blood vessel regions (i.e., masking regions) input together with the target frame image of the machine learning model 510 may be determined based on a predetermined frame range or a predetermined number. For example, if the current target frame image number is #50 and the frame range of the blood vessel region to be applied is 10 frames, a plurality of blood vessel regions extracted from each of the frame images #51 to #60 may be applied to the machine learning model together with the target frame image #50. As another example, if the current target frame image is #50 and the number of blood vessel regions to be applied is 5, five blood vessel regions extracted from each of the five frame images numbered close to the frame number #50, among the frame images #51 or above, may be applied to the machine learning model along with the target frame image #50.

If some selected blood vessel regions are applied to the machine learning model, instead of applying the plurality of blood vessel regions extracted from each of all frame images with previous numbers to the machine learning model, computational speed can be greatly improved and computing resources can be reduced with little deterioration in accuracy.

Meanwhile, due to the heartbeat, the position of the blood vessel region in some of the frame images may appear differently. If the position of the blood vessel region (e.g., the pixel coordinate region) in some frame images is different, it may be difficult to compute an accurate blood flow velocity. Accordingly, image correction may be performed as illustrated in FIG. 6, which will be described below, so that the positions of the blood vessel region (e.g., pixel coordinate region) illustrated in each of the plurality of frame images are aligned.

Figure 6:
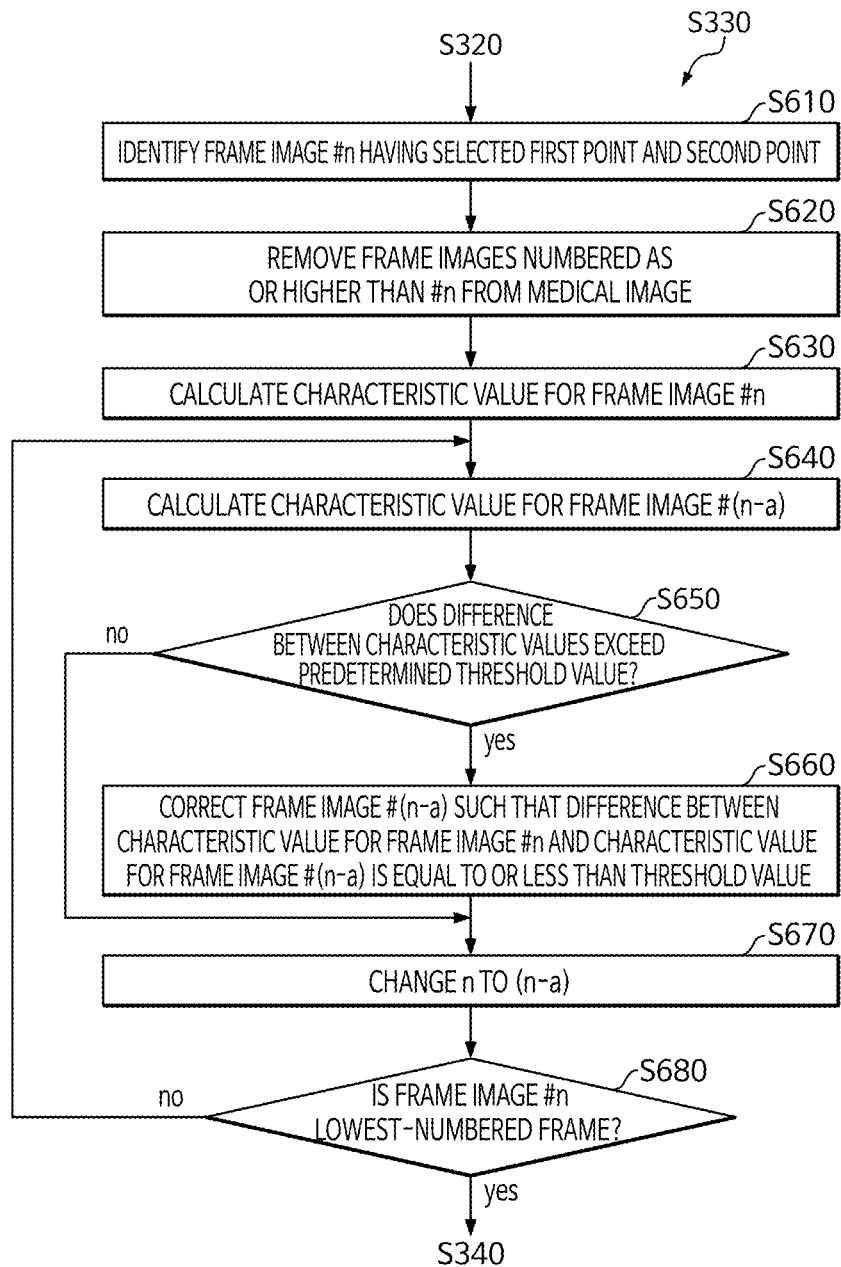
FIG. 6 is a flowchart provided to explain the operation S330 of FIG. 3 in more detail.

FIG. 6 is a flowchart provided to explain the operation S330 of FIG. 3 in more detail. The processor may identify a frame image #n having the selected first and second points from the medical image, at S610. Here, #n may refer to the number of the frame image having the selected first and second points. The processor may remove the frame image numbered higher than the frame image #n from the medical image to filter the frame images included in the medical image, at S620.

The processor may compute a spatial characteristic value for the frame image #n, at S630. The spatial characteristic value may be associated with the shape characteristic of the frame image. The processor may compute a characteristic value for the frame image #n using a function capable of computing a characteristic value for a space, such as an affine matrix-related function, a grid distortion-related function, an elastic transformation-related function, etc.

The processor may compute a characteristic value for the frame image #n−a, at S640. Here, a may be determined based on an interval sampled by a natural number. For example, the processor may compute a spatial characteristic value for the frame image #n−a using a function capable of computing a characteristic value for a space, such as an affine matrix-related function, a grid distortion-related function, an elastic transformation-related function, etc. As another example, the processor may apply the frame image #n−a to the machine learning model configured to compute a spatial characteristic value for an image so as to compute a spatial characteristic value for the frame image #n−a.

The processor may determine whether a difference between the characteristic value of the frame image #n and the characteristic value of the frame image #n−a exceeds a predetermined threshold value, at S650.

In response to the determination that the difference between the characteristic value of the frame image #n and the characteristic value of the frame image #n−a is equal to or less than a threshold value, the processor may update n by subtracting the natural number a from n, at S670.

On the other hand, in response to the determination that the difference between the characteristic value for the frame image #n and the characteristic value for the frame image #n−a exceeds the predetermined threshold, the processor may correct at least one of the frame image #n−a or the frame image #n such that the difference between the characteristic value for the frame image #n and the characteristic value for the frame image #n−a is equal to or less than the threshold value, at S660. The processor may update n by subtracting the determined natural number a from n, at S670.

The processor may determine whether the updated frame image #n is a lowest-numbered frame image, at S680. The processor may repeat the processes from S640 in response to the determination that the updated frame image #n is not the lowest-numbered frame image. If the process repeats from step S640, the updated spatial characteristic value of the frame image #n and the spatial characteristic value of the frame image #n−a may be compared, and based on the comparison result, it may be determined that at least one of the frame image #n−a or the frame image #n is corrected.

Meanwhile, the correction on the frame image may be performed while changing the target frames for analysis from low to high frame numbers. For example, a lowest-numbered frame image may be selected first, and a frame image number increased by a from the lowest-numbered frame image is selected as an image for comparison, and by comparing the spatial characteristic values of the two images, the frame image correction may be determined based on the comparison result. Then, the spatial characteristic values may be compared between frame numbers increased by a, and the correction for the increased frame image numbers may be determined based on the comparison result.

According to the method according to FIG. 6, the correction of the frame image may be determined based on the spatial characteristic values of adjacent frames, and the positions of the blood vessel regions included in each of the plurality of frame images may be aligned.

According to some aspects, the processor may apply a plurality of frame images to a machine learning model capable of correcting a frame image so as to correct at least one of the plurality of frames. The machine learning model capable of correcting the frame image may be configured to correct at least one frame image such that a difference in spatial characteristic values between adjacent frame images is equal to or less than a predetermined threshold value. In addition, the machine learning model capable of correcting the image may be a model trained based on a plurality of training data sets. The plurality of training data sets may include a plurality of pieces of training data and a plurality of ground-truth labels. The training data may include a pair of frame images having frame numbers adjacent to each other, and the ground-truth label may include at least one corrected frame image of the pair of frame images. The machine learning model for frame image correction may analyze the training data and output a corrected frame image. A loss between the output frame image and the corrected image included in the ground-truth label may be computed, and the computed loss may be fed back to the machine learning model such that the weight of the node included in the machine learning model may be adjusted.

Figure 7:
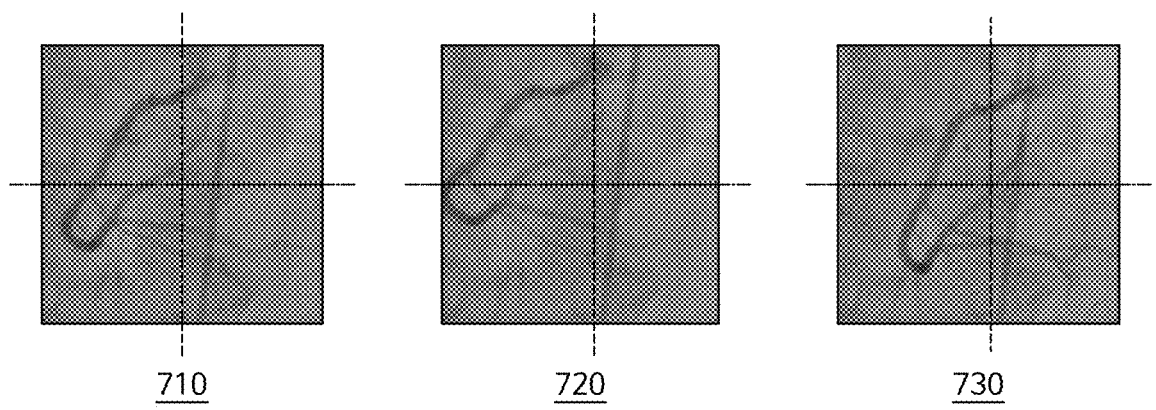
FIG. 7 is a diagram illustrating an original frame image.
Figure 8:
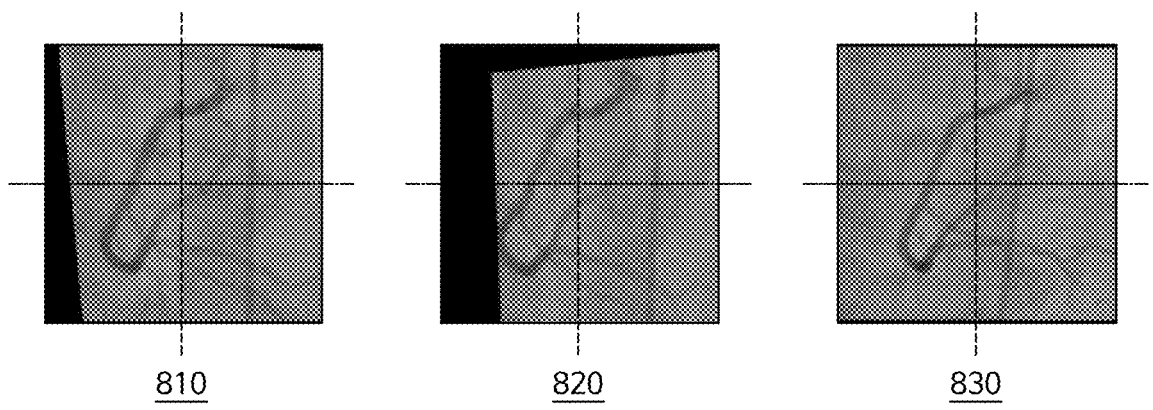
FIG. 8 is a diagram illustrating a corrected frame image.

FIG. 7 is a diagram illustrating an original frame image, and FIG. 8 is a diagram illustrating a corrected frame image. In FIGS. 7 and 8, it may be assumed that a frame image 710 and 810 on the left hand side has the lowest frame image number and a frame image 730 and 830 on the right hand side has the highest frame image number.

As illustrated in FIG. 7, it can be seen that the position of the blood vessel region included in the first frame image 710 and the position of the blood vessel region included in the second frame image 720 clearly differ from each other based on the pixel coordinates. In addition, it can be seen that the position of the blood vessel region included in the second frame image 720 and the position of the blood vessel region included in the third frame image 730 clearly differ from each other based on the pixel coordinates.

On the other hand, the frame images 810 to 830 illustrated in FIG. 8 are examples of the corrected frame images, and it can be seen that the position of the blood vessel region included in the fourth frame image 810 and the position of the blood vessel region included in the fifth frame image 820 are aligned based on pixel coordinates as illustrated in FIG. 8. In addition, it can be seen that the position of the blood vessel region included in the fifth frame image 820 and the position of the blood vessel region included in the sixth frame image 830 are aligned based on pixel coordinates.

Figure 9:
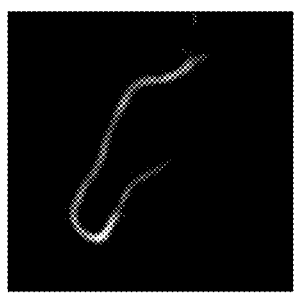
FIG. 9 is a diagram illustrating blood vessel regions extracted from a corrected frame image.
Figure 9:
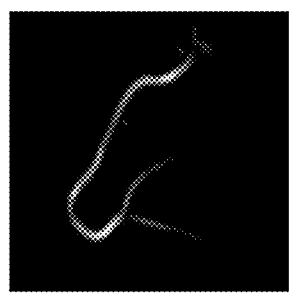
Figure 9:
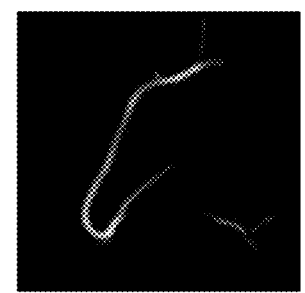

FIG. 9 is a diagram illustrating blood vessel regions 910 to 930 extracted from a corrected frame image. As illustrated in FIG. 9, it may be seen that the positions of the blood vessel regions 910 to 930 extracted from each corrected frame image are almost identical to each other based on pixel coordinates. Accordingly, if the blood flow velocity is computed based on the corrected frame image, the accuracy may be improved.

Figure 10:
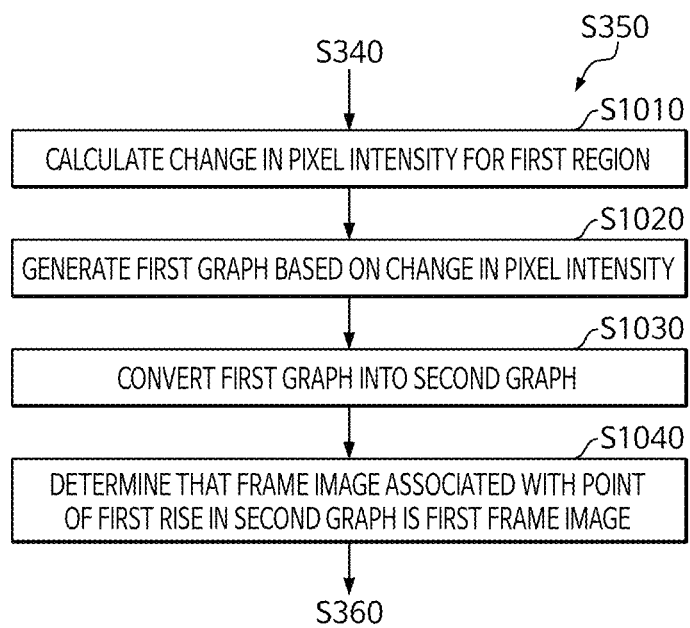
FIG. 10 is a flowchart provided to explain the operation S350 of FIG. 3 in more detail.

FIG. 10 is a flowchart provided to explain the operation S350 of FIG. 3 in more detail. The processor may compute a change in pixel intensity for a plurality of first regions extracted from a plurality of frame images, at S1010. The processor may compute a plurality of pixel intensities from the plurality of first regions, and compute a change in pixel intensity for the first region based on the computed plurality of pixel intensities and frame numbers. For example, the pixel intensity may be intensity with respect to saturation and/or brightness with respect to a pixel. As another example, the pixel intensity may be the probability that the pixel is a blood vessel. The processor may generate a first graph based on the change in pixel intensity, at S1020. The processor may generate the first graph, in which the first axis represents a frame number and the second axis represents a pixel intensity. The first graph may be a graph based on multi-order term.

The processor may convert the first graph into a second graph based on at least one of the zeroth-order term and the first-order term, at S1030. That is, the processor may convert the first graph based on multi-order term into the second graph based on at least one of the zeroth-order term and the first-order term.

The processor may identify a point at which the pixel value rises for the first time in the second graph, and determine that a frame image associated with the identified rising point is the first frame image, at S1040. Additionally, if the contrast agent arrives at the blood vessel, the blood vessel region in the medical image where the contrast agent arrives may have a change in at least one of the saturation or brightness. In this way, the change in saturation and brightness may be measured as a change in pixel intensity, and based on the change in pixel intensity, a frame image showing a predetermined size of change in pixel intensity in the first region may be determined to be the first frame image. In order to accurately determine a frame image that shows the predetermined size of change in pixel intensity, the processor may convert the first graph based on the multi-order term into the second graph based on at least one of the zeroth-order term or the first-order term. A second frame image associated with the contrast agent arriving at the second point may be determined in the similar manner as the method described above with reference to FIG. 10. Specifically, the processor may compute a change in pixel intensity for a plurality of second regions extracted from a plurality of frame images and generate a third graph based on the change in pixel intensity. The processor may convert the third graph into a fourth graph based on at least one of the zeroth-order term and the first-order term. The processor may identify a point at which the pixel value rises for the first time in the fourth graph, and determine a frame image associated with the identified rising point to be the second frame image.

Figure 11:
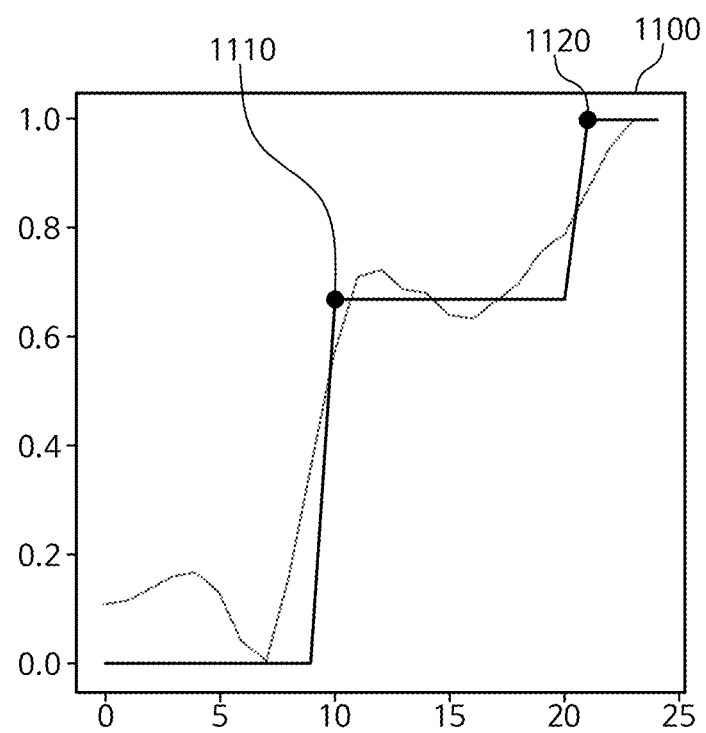
FIG. 11 is a diagram illustrating a graph associated with the change in pixel intensity.

FIG. 11 is a diagram illustrating a graph associated with the change in pixel intensity. In FIG. 11, the graph including a curve may be the first graph based on the multi-order term, and the stepped graph may be the second graph based on at least one of the zeroth-order and the first-order term. The second graph may be a graph converted based on the first graph.

In the second graph, it may be determined that a frame image numbered in association with a point 1110 at which the pixel value rises for the first time is the frame image associated with the contrast agent arriving at the first point or the second point. FIG. 11 illustrates frame image #10 as a frame image associated with the point 1110 at which the pixel value rises for the first time. The frame image #10 may be the frame image associated with the contrast agent arriving at the point.

Additionally or alternatively, a frame image associated with a point 1120 at which the pixel value rises for the second time may be determined. That is, the frame image associated with the point 1120 at which the pixel value rises for the second time may be determined based on the change in pixel intensity. FIG. 11 illustrates frame image #20 as a frame image associated with the point 1120 at which the pixel value rises for the second time. The frame image #20 may be a frame image associated with the blood vessel full of contrast agent.

Additionally, the pixel intensity may change a first time by a predetermined first size in the region where the contrast agent arrives, and may change a second time by a predetermined second size as the region is full of contrast agent. In FIG. 11, the point associated with 1110 may be the point where the change in pixel intensity occurs for the first time, and the point associated with 1120 may be the point where the change in pixel intensity occurs for the second time.

According to some aspects, the processor may determine a third frame image of the first point full of contrast agent based on a change in pixel intensity in the first region, and determine a fourth frame image of the second point full of contrast agent based on a change in pixel intensity in the second region. The processor may compute the blood flow velocity at the time the contrast agent is full, based on a time interval between the third frame image and the fourth frame image and a distance between the first point and the second point. The blood flow velocity computed based on the time point at which the contrast agent is full, and the blood flow velocity computed based on the time point at which the contrast agent arrives, may be distinguished from each other and provided to the user. For example, a first blood flow velocity computed based on the time point at which the contrast agent is arrives, and a second blood flow velocity computed based on the time point at which the contrast agent is full, may be provided to the user together.

Figure 12:
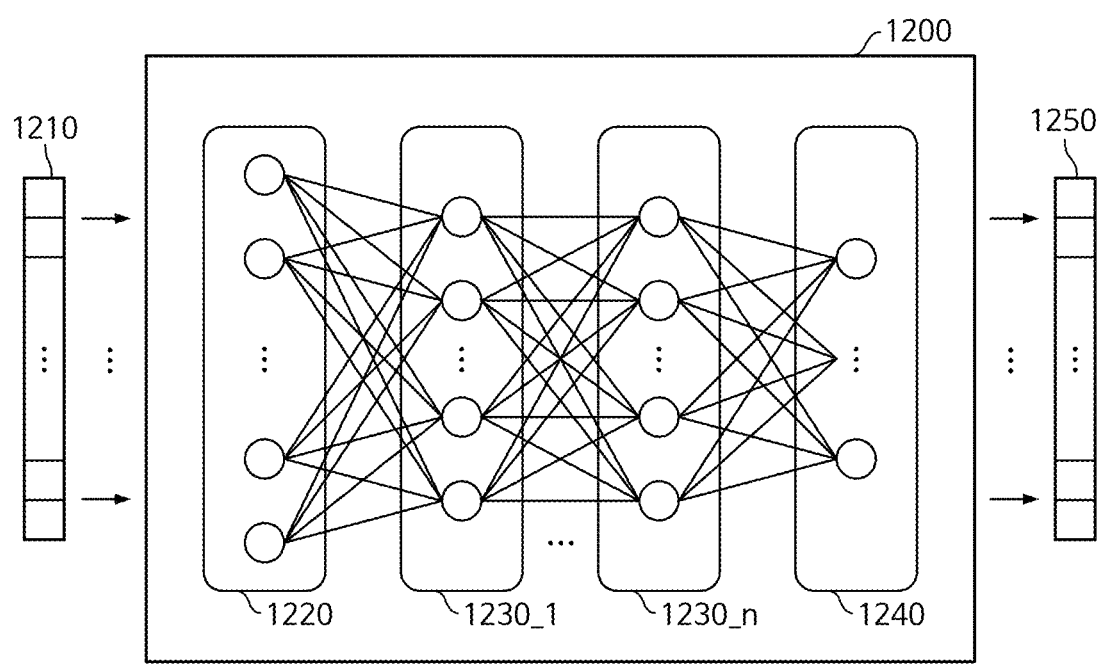
FIG. 12 is an example diagram illustrating an artificial neural network model.

FIG. 12 is an example diagram illustrating an artificial neural network model 1200. In the machine learning technology and cognitive science, the artificial neural network model 1200 as an example of the machine learning model used in an aspect of the present disclosure refers to a statistical learning algorithm implemented based on a structure of a biological neural network, or to a structure that executes such algorithm.

The artificial neural network model 1200 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 1200 may include any probability model, neural network model, etc., that is used in artificial intelligence training methods such as machine learning and deep learning.

The machine learning model for extracting a blood vessel region from the frame image described above may be generated in the form of the artificial neural network model 1200. For example, the artificial neural network model 1200 may receive a frame image, determine a blood vessel region from the frame image, perform masking processing on the determined blood vessel region, and output the result. In some aspects, the machine learning model for correcting the frame image described above may be generated in the form of the artificial neural network model 1200.

The artificial neural network model 1200 may be implemented as a multi-layer perceptron (MLP) formed of multi-layer nodes and connections between them. For example, the artificial neural network model 1200 may be implemented using one of various artificial neural network model structures including the MLP. As illustrated in FIG. 12, the artificial neural network model 1200 includes an input layer 1220 to receive an input signal or data 1210 from the outside, an output layer 1240 to output an output signal or data 1250 corresponding to the input data, and (n) number of hidden layers 1230_1 to 1230_$n$ (where n is a positive integer) positioned between the input layer 1220 and the output layer 1240 to receive a signal from the input layer 1220, extract the features, and transmit the features to the output layer 1240. In an example, the output layer 1240 receives signals from the hidden layers 1230_1 to 1230_$n$ and outputs the signals to the outside.

The method for training the artificial neural network model 1200 may include a supervised learning method that trains to be optimized for problem solving by input of teacher signals (correct answers), an unsupervised learning method that does not require a teacher signal, and semi-supervised learning that trains to solve a problem by input of teacher signals (correct answers) and comparator signals. The information processing system may train the artificial neural network model 1200 using a training set including a plurality of cardiovascular images obtained by capturing images of the cardiovascular system.

As described above, the input layer 1220 and the output layer 1240 of the artificial neural network model 1200 are respectively matched with a plurality of output variables corresponding to a plurality of input variables, and as the synaptic values between nodes included in the input layer 1220, and the hidden layers 1230_1 to 1230_$n$, and the output layer 1240 are adjusted, training can be processed to extract a correct output corresponding to a specific input. Through this training process, the features hidden in the input variables of the artificial neural network model 1200 can be confirmed, and the synaptic values (or weights) between the nodes of the artificial neural network model 1200 can be adjusted so that there can be a reduced error between the target output and the output variable computed based on the input variable. The blood vessel region may be extracted from the received frame image using the trained artificial neural network model 1200.

The flowchart and description above are merely examples and may be implemented differently in some examples. For example, in some examples, the order of respective steps may be changed, some steps may be repeatedly performed, some steps may be omitted, or some steps may be added.

The method described above may be provided as a computer program stored in a computer-readable recording medium for execution on a computer. The medium may be a type of medium that continuously stores a program executable by a computer, or temporarily stores the program for execution or download. In addition, the medium may be a variety of recording means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, etc. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies depending on design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or optical data storage devices, etc. The instructions may be executable by one or more processors, and may cause the processor(s) to perform certain aspects of the functions described in the present disclosure.

When implemented in software, the techniques may be stored on a computer-readable medium as one or more instructions or codes, or may be transmitted through a computer-readable medium. The computer-readable media include both the computer storage media and the communication media including any medium that facilitates the transmission of a computer program from one place to another. The storage media may also be any available media that may be accessible to a computer. By way of non-limiting example, such a computer-readable medium may include RAM, ROM, EEPROM, CD-ROM or other optical disk storage, magnetic disk storage or other magnetic storage devices, or any other media that can be used to transmit or store desired program code in the form of instructions or data structures and can be accessible to a computer. In addition, any connection is properly referred to as a computer-readable medium.

For example, if the software is sent from a website, server, or other remote sources using coaxial cable, fiber optic cable, twisted pair, digital subscriber line (DSL), or wireless technologies such as infrared, wireless, and microwave, the coaxial cable, the fiber optic cable, the twisted pair, the digital subscriber line, or the wireless technologies such as infrared, wireless, and microwave are included within the definition of the medium. The disks and the discs used herein include CDs, laser disks, optical disks, digital versatile discs (DVDs), floppy disks, and Blu-ray disks, where disks usually magnetically reproduce data, while discs optically reproduce data using a laser. The combinations described above should also be included within the scope of the computer-readable media.

The software module may reside in RAM memory, flash memory, ROM memory, EPROM memory, EEPROM memory, registers, hard disk, removable disk, CD-ROM, or any other form of storage medium known. An exemplary storage medium may be connected to the processor such that the processor may read or write information from or to the storage medium. Alternatively, the storage medium may be integrated into the processor. The processor and the storage medium may exist in the ASIC. The ASIC may exist in the user terminal. Alternatively, the processor and storage medium may exist as separate components in the user terminal.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or apparatus, and storage may be similarly influenced across a plurality of apparatus. Such apparatus may include PCs, network servers, and portable apparatus.

Although the present disclosure has been described in connection with some examples herein, various modifications and changes can be made without departing from the scope of the present disclosure, which can be understood by those skilled in the art to which the present disclosure pertains. In addition, such modifications and changes should be considered within the scope of the claims appended herein.

The invention claimed is:

1. A method for identifying a blood flow velocity, the method being performed by one or more processors and comprising:
   receiving a user input to select a plurality of points from a medical image obtained by capturing an image of a blood vessel injected with a contrast agent, wherein the selected plurality of points comprises a first point and a second point;
   extracting a plurality of blood vessel regions from a plurality of frame images included in the medical image, wherein the extracting the plurality of blood vessel regions from the plurality of frame images comprises:

identifying, among the plurality of frame images included in the medical image, a frame image having the selected first and second points;

determining that, among the entire frame images included in the medical image, a plurality of frame images numbered as or lower than a number corresponding to the identified frame image are target images for analysis; and extracting the plurality of blood vessel regions from at least one of the plurality of frame images determined to be the target images for analysis;

determining, in the extracted plurality of blood vessel regions, a plurality of first regions associated with the first point and a plurality of second regions associated with the second point;

determining, among the plurality of frame images, a first frame image with the contrast agent arriving at the first point, based on a change in pixel intensity for each of the plurality of first regions;

determining, among the plurality of frame images, a second frame image with the contrast agent arriving at the second point, based on a change in pixel intensity for each of the plurality of second regions;

identifying, based on a time interval between the first frame image and the second frame image and based on a distance between the first point and the second point, the blood flow velocity from the first point to the second point; and generating an indication of the blood flow velocity from the first point to the second point.

2. The method according to claim 1, wherein the determining that the plurality of frame images are the target images for analysis comprises:

sampling a plurality of frame images numbered as or lower than the number corresponding to the identified frame image; and determining that the plurality of sampled frame images are the target images for analysis.

3. The method according to claim 1, wherein the extracting the plurality of blood vessel regions from the plurality of frame images comprises:

applying each of the plurality of frame images to a machine learning model to extract the plurality of blood vessel regions, and wherein the machine learning model is configured to perform an operation based on supervised learning for a highest-numbered frame image of the plurality of frame images, and perform an operation based on semi-supervised learning for a frame image numbered lower than the highest-numbered frame image.

4. The method according to claim 3, wherein the applying each of the plurality of frame images to the machine learning model to extract the plurality of blood vessel regions comprises:

applying the highest-numbered frame image of the plurality of frame images to the machine learning model to extract a blood vessel region included in the highest-numbered frame image;

sequentially determining that, based on an ascending order of frame image numbers, each of a plurality of frame images numbered lower than the highest-numbered frame image is a target frame image to be applied; and applying, to the machine learning model, at least one blood vessel region extracted from each of at least one frame image numbered higher than the determined target frame image, and the determined target frame image, and wherein the machine learning model is configured to extract the blood vessel region from the target frame image based on at least one blood vessel region extracted from each of at least one frame image numbered higher the target frame image.

5. The method according to claim 4, wherein the applying the at least one blood vessel region and the determined target frame image to the machine learning model comprises:

selecting, among the frame images numbered higher the target frame image, at least one frame image included in a predetermined frame range or in a predetermined number of frame images; and applying, to the machine learning model, the at least one blood vessel region extracted from each of the at least one selected frame image.

6. The method according to claim 1, further comprising:

prior to the determining the first frame image with the contrast agent arriving at the first point, correcting at least one of the plurality of frame images such that blood vessel regions included in each of the plurality of frame images are positioned within a threshold distance range.

7. The method according to claim 6, wherein the correcting the at least one of the plurality of frame images comprises:

identifying a spatial characteristic value for each of the plurality of frame images; and correcting at least one frame image such that a difference in spatial characteristic values between adjacent frame images is equal to or less than a predetermined threshold value.

8. The method according to claim 6, wherein:

the correcting the at least one of the plurality of frame images comprises applying, to a machine learning model, the plurality of frame images to correct at least one of the plurality of frame images, and the machine learning model is configured to correct at least one frame image such that a difference in spatial characteristic values between adjacent frame images is equal to or less than a predetermined threshold value.

9. The method according to claim 1, wherein the determining the first frame image with the contrast agent arriving at the first point comprises:

identifying a change in pixel intensity for the first region, of the plurality of first regions, determined in each of the plurality of frame images; and determining that, based on the identified change in pixel intensity for the first region, a frame image showing a predetermined size of change in pixel intensity is the first frame image.

10. The method according to claim 9, wherein the determining that the frame image showing the predetermined size of change in pixel intensity is the first frame image comprises:

generating a first graph associated with the change in pixel intensity for the first region;

converting the first graph into a second graph based on at least one of a zeroth-order term or a first-order term;

identifying a point at which a pixel value rises for the first time in the second graph; and determining that a frame image associated with the identified rising point is the first frame image.

11. The method according to claim 1, wherein the determining the plurality of first regions associated with the first point and the plurality of second regions associated with the second point comprises:
  determining that a first-sized corresponding region including the first point is each of the plurality of first regions; and
  determining that a second-sized corresponding region including the second point is each of the plurality of second regions.

12. A method for extracting a blood vessel region, the method being performed by one or more processors and comprising:
  receiving a medical image obtained by capturing an image of a blood vessel injected with a contrast agent;
  determining, from the medical image, a plurality of frame images for analysis; and
  applying the plurality of frame images to a machine learning model to extract a plurality of blood vessel regions from the plurality of frame images;
  determining, among the plurality of frame images, a first frame image with the contrast agent arriving at the first point;
  determining, among the plurality of frame images, a second frame image with the contrast agent arriving at the second point;
  identifying, based on a time interval between the first frame image and the second frame image and based on a distance between the first point and the second point, the blood flow velocity from the first point to the second point; and
  generating an indication of the blood flow velocity from the first point to the second point,
  wherein the machine learning model is configured to perform an operation based on supervised learning for a highest-numbered frame image of the plurality of frame images to extract a blood vessel region, and perform an operation based on semi-supervised learning for a frame image numbered lower than the highest-numbered frame image to extract a blood vessel region.

13. The method according to claim 12, further comprising:
  extracting the plurality of blood vessel regions from the plurality of frame images by:
  applying the highest-numbered frame image of the plurality of frame images to the machine learning model to extract a blood vessel region included in the highest-numbered frame image;
  sequentially determining that, based on an ascending order of frame image numbers, each of a plurality of frame images numbered lower than the highest-numbered frame image is a target frame image to be applied; and
  applying, to the machine learning model, at least one blood vessel region extracted from each of at least one frame image numbered higher than the determined target frame image, and the determined target frame image, and
  wherein the machine learning model is configured to extract the blood vessel region from the target frame image based on at least one blood vessel region extracted from each of at least one frame image numbered higher the target frame image.

14. A non-transitory computer-readable medium storing instructions that, when executed, cause performance of the method according to claim 1.

15. An information processing system, comprising:
  a memory; and
  one or more processors coupled to the memory and configured to execute one or more computer-readable programs included in the memory, wherein
  the one or more computer-readable programs include instructions that, when executed by the one or more processors, cause the information processing system to:
    receive a user input to select a plurality of points from a medical image obtained by capturing an image of a blood vessel injected with a contrast agent, wherein the selected plurality of points comprises a first point and a second point;
    extract a plurality of blood vessel regions, from a plurality of frame images included in the medical image, by:
      identifying, among frame images included in the medical image, a frame image having the selected first and second points;
      determining that, among the frame images included in the medical image, a subset of frame images are target images for analysis, wherein a frame number corresponding to each frame image of the subset of frame images is less than or equal to a frame number corresponding to the identified frame image; and
      extracting the plurality of blood vessel regions from at least one of the subset of frame images determined to be the target images for analysis;
    determine, in the extracted plurality of blood vessel regions, a plurality of first regions associated with the first point and a plurality of second regions associated with the second point;
    determine, among the plurality of frame images, a first frame image with the contrast agent arriving at the first point, based on a change in pixel intensity for each of the plurality of first regions;
    determine, among the plurality of frame images, a second frame image with the contrast agent arriving at the second point, based on a change in pixel intensity for each of the plurality of second regions;
    identify, based on a time interval between the first frame image and the second frame image and based on a distance between the first point and the second point, a blood flow velocity from the first point to the second point; and
    generate an indication of the blood flow velocity from the first point to the second point.

16. The information processing system according to claim 15, wherein the instructions, when executed by the one or more processors, cause the information processing system to determine that the plurality of frame images are the target images for analysis by:
  sampling, based on the frame number corresponding to the identified frame image, a subset of frame images; and
  determining that the subset of sampled frame images are the target images for analysis.

17. The information processing system according to claim 15, wherein the instructions, when executed by the one or more processors, cause the information processing system to extract the plurality of blood vessel regions from the plurality of frame images by:
  applying each of the subset of frame images to a machine learning model to extract the plurality of blood vessel regions, and wherein the machine learning model is configured to perform an operation based on a first learning algorithm for at least one first frame image of the subset of frame images, and perform an operation based on a second learning algorithm for at least one second frame image of the subset of frame images.

18. The information processing system according to claim 17, wherein the first learning algorithm comprises at least one of a supervised learning algorithm or a semi-supervised learning algorithm, and wherein the second learning algorithm comprises at least one of an unsupervised learning algorithm or a reinforcement learning algorithm.

19. The information processing system according to claim 17, wherein the at least one first frame image of the subset of frame images comprises the identified frame image.

20. The information processing system according to claim 17, wherein the instructions, when executed by the one or more processors, cause the information processing system to:

select, among a second subset of frame images included in the medical image, at least one frame image included in a predetermined frame range or in a predetermined number of frame images; and apply, to the machine learning model, at least one blood vessel region extracted from each of the at least one selected frame image.

* * * * *